United States Patent [19]

Samuelsen

[11] Patent Number: 4,867,748

[45] Date of Patent: Sep. 19, 1989

[54] DRESSING WITH HYDROCOLLOID

[75] Inventor: Peter Samuelsen, Rungsted Kyst, Denmark

[73] Assignee: Coloplast A/S, Espergaerde, Denmark

[21] Appl. No.: 107,157

[22] Filed: Oct. 13, 1987

[30] Foreign Application Priority Data

Oct. 17, 1986 [DK] Denmark ............................. 4976/86

[51] Int. Cl.⁴ ............................................. A61F 5/44
[52] U.S. Cl. .................................. 604/336; 128/156; 604/344
[58] Field of Search ................. 128/156; 604/336, 344

[56] References Cited

U.S. PATENT DOCUMENTS

| 2,649,088 | 8/1953 | Sigg ..................................... 128/156 |
| 4,213,458 | 7/1980 | Nolan et al. ......................... 604/344 |
| 4,231,369 | 11/1980 | Sorensen et al. .................... 604/336 |
| 4,700,699 | 10/1987 | Tollerud et al. ..................... 128/156 |

FOREIGN PATENT DOCUMENTS

| 2387643 | 12/1978 | France ................................. 604/344 |
| 2082916 | 3/1982 | United Kingdom ................ 604/344 |

Primary Examiner—Albert W. Davis, Jr.
Attorney, Agent, or Firm—Armstrong, Nikaido, Marmelstein, Kubovcik & Murray

[57] ABSTRACT

A dressing comprising a dressing containing a water-soluble or water-swellable hydrocolloid, a water-insoluble, viscous, elastomeric binder and optionally also a tackifier resin, is bevelled along all outer edges and optionally also, if annular, along the inner edge.

5 Claims, 1 Drawing Sheet

DRESSING WITH HYDROCOLLOID

FIELD OF THE INVENTION

The present invention relates to a dressing of the kind comprising a skin-friendly, water absorbent sealing pad adhering to skin and mucous membranes and having a predetermined shape and size, said dressing consisting of a water-soluble or water-swellable hydrocolloid dispersed in or admixed with a water-insoluble, viscous, elastomeric binder and/or a tackifier resin and/or other adjuvants, said sealing pad on one surface being firmly connected to a non-adhesive, water-tight cover layer and on the other surface being provided with a detachable protective cover, the sealing pad extending to the outer edges of the cover layer.

BACKGROUND OF THE INVENTION

An important use thereof is as dressings, e.g. for the absorption of wound secretions for instance by coverage of ulcers and burns. A further important use is as prophylactic dressings for avoidance of blisters and wounds from shear and friction. Other important fields of use are as sealing pads for securing ostomy equipment such as ostomy bags, drains and/or collecting bags for drainage from surgical wounds and incontinence equipment. The dressings are also used with healing substances for wound care incorporated therein.

In the former case a rather heavy uptake of liquids takes place in the sealing pad because of the hydrocolloid therein, and sooner or later this will cause the sealing pad to loose its ability of sealing to the body of the patient. When used for fastening ostomy or drainage equipment the same will occur, first due to the uptake of sweat from the skin around the aperture of the sealing pad through which the stoma or drain protrudes into a collecting bag or similar device, and secondly because intestinal secretion or wound secretion may penetrate into the edges of the sealing pad around the aperture in question; it is hereby remarked that an important part of the function of such dressings when used as sealing pads for ostomy equipment is to tighten against the stoma in order to prevent aggressive (enzyme-containing) secretions from the artificial anus from entering into contact with the skin of the patient.

It is a well-known drawback in such dressings that the material constituting the sealing pad has a tendency to flow along the edges thereof, partly influenced by the absorbed aqueous secretions, but especially under the influence of pressure since the material of the sealing pad even at body temperature (approx. 37° C.) is so plastic that even weak pressures for instance from folds of the skin will cause the substance to flow.

When the sealing pad material flows from under the cover layer, it will stick to garments or bed linen, which is unhygienic and is also inconvenient for the nursing staff.

In using such dressings in wound care it has therefore been usual to place a pressure sensitive tape, for instance a microporous tape, on the outer edges of the dressing and extending a suitable length, for instance 1-2 cm from the edge at all sides. This, however, is a price-raising measure and will also increase the time consumption of the nursing staff for bandaging. Also in ostomy equipment it is well-known, for instance from U.S. Pat. No. 4,213,458, corresponding to Danish Patent Specification No. 146,466, and from various commercial ostomy bags to provide ostomy sealing rings with a porous sheet material such as a microporous tape over and around the outer edge in order to prevent the material of the sealing pad from flowing out and to further strengthen the adhesion. This contributes to make the ostomy equipment in question more expensive and cannot be used on the inner part of the sealing pad adjacent the ostomy aperture.

It has been attempted to solve this problem by means of the dressing "DuoDERM" ® sold by the company ConvaTec, USA, in which the sealing pad only extends to a distance of about 1 cm from the edge of the watertight cover layer, and which on the part thereof where the sealing pad is not present is provided with a thin layer of a pressure sensitive adhesive. A disadvantage of this construction is first that there is a sharp transition of thickness from the sealing pad to the pressure-sensitive adhesive, secondly that the latter is not water-absorbent which, i.a., involves the same inconvenience in the removal thereof as does the removal of ordinary plasters and thirdly that it is much more expensive to manufacture.

As the area of the skin to which the dressing or ostomy equipment is attached may often be very sensitive, the use of pressure sensitive adhesives that are not water absorbing should be avoided.

BRIEF DESCRIPTION OF THE INVENTION

It has now been surprisingly found that the said drawbacks may be remedied if according to the invention the sealing pad at least along all outer edges is bevelled in the thickness dimension such that its thickness adjacent the edge does not exceed ¼ of the thickness of the sealing pad in its non-bevelled portions. If the dressing is ring-shaped and especially intended for securing ostomy or drainage equipment and is provided with an aperture for engaging a stoma or a drain, the sealing pad according to the invention may also be bevelled and have reduced thickness along the edge of said aperture.

A series of advantages are obtained by this bevelling of the edges of dressings and ostomy sealing pads. Plasticizing of the adhesive material of the sealing pad by warming due to contact with the skin and the application of pressure will cause the plasticized adhesive to flow to the portion of smaller thickness of material in the bevel. This will normally be sufficient to prevent the adhesive material from flowing outside the cover layer and smudging garments or bed linen. Thus, the costs of tapes and the time consumption involved in the mounting thereof are saved. This applies to the outer edges of dressings as well as ostomy sealing rings, and to a certain degree also to the inner edge—the edge of the aperture for the stoma or the drain in ring-shaped pads for ostomy and drainage equipment. Here, however, a further advantage is obtained, especially in ostomy sealing pads.

The inner edge of such rings will absorb liquid that might leak from the stoma instead of entering the ostomy bag. This causes the inner edge of the ring to swell to a higher degree than the remaining parts of the pad and more quickly become less adhesive to the skin, which will entail a highly undesired contact between the liquid and the skin. The degree of uptake of liquid into the pad from the inner edge of the annular structure is, however, proportional to the thickness of the edge and when due to the bevel this is smaller than normal, the sealing effect will last longer and the lifetime of the sealing ring will be increased.

When the tendency of the sealing disc to flow out from the cover layer along the outer edge of the dressing is reduced, the use of tape on and around the outer edge to fasten the dressing or fastening the sealing ring becomes unnecessary. The bevelled thin edge portions of the dressing or sealing pad are more than is the remainder thereof and thereby offer an especially good adhesion which is on a par with that obtained by strengthening with tape comprising a self-adhesive sealant.

BRIEF DESCRIPTION OF THE DRAWINGS

In the following the dressing according to the invention will be described with reference to the drawing in which.

DETAILED DESCRIPTION OF VARIOUS EMBODIMENTS OF THE INVENTION

In both of the figures the thickness dimension is not necessarily in correct proportion to the dimension of width.

Figure 1:
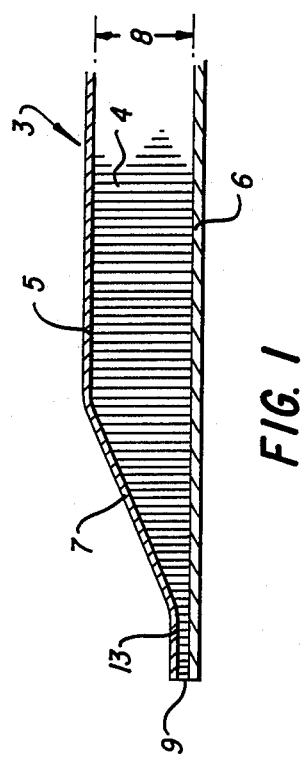
FIG. 1 shows a partial cross-section of such a dressing in the form of a skin sheet.

A dressing 3 shown in FIG. 1 has a main component comprising a sealing pad 4 made from a skin-friendly, water absorbent adhesive material consisting of a water-soluble or water-swellable hydrocolloid blended with or dispersed in a water-insoluble, viscous, elastomeric binder and possibly also an adhesive resin and/or other adjuvants.

On the upper surface the sealing pad is firmly connected, e.g. by virtue of its pressure-sensitive properties, to a cover layer 5 and on the under side with a detachable protective cover 6, e.g. of siliconized paper.

The dressing may be of any known kind. The cover layer is preferably a film of water-tight (and hence water-insoluble) material, e.g. a polyurethane, polyethylene, polyester or polyamide film, or a thin foam material of for instance one of the same materials. The cover layer may also be laminated, e.g. when it has to have a high mechanical strength when used for connecting the dressing to other objects.

The protective cover 6 may for instance be siliconized paper. It does not need to have the same contour as the sealing pad 4 and the cover layer 5, e.g. a number of dressings may be attached to a larger sheet of protective cover; this sheet is not present on the dressing according to the invention when in use and therefore is not a proper part of the dressing.

The sealing pad may be of any known type of the hydrocolloid-containing, liquid-absorbing kind. As an example may be mentioned the dressing known from U.S. Pat. No. 3,339,546 in which the adhesive binder composition is a mixture of a water-soluble or swellable hydrocolloid admixed with a water-soluble, viscous, rubber-like elastic binder. As examples of the hydrocolloid the specification mentions polyvinyl alcohol, pectin, gelatin, carboxymethyl cellulose, carbowax and carboxypolymethylene; and as examples of the viscous binder natural rubber (caoutchouc), silicone rubber, acrylonitrile rubber, polyurethane rubber, sucrose acetate isoburytate and polyisobutylene, amongst which the latter is preferred.

In connection with the present invention it is, however, preferred to use a sealing pad as the one described in the Danish Patent Specifications Nos. 147,034 and 147,035, corresponding to the U.S. Pat. Nos. 4,231,369 and 4,367,732. It consists of (I) a continuous phase containing a physically cross-linked elastomer consisting of one or more styrene-olefine-styrene block copolymers, a hydrocarbon tackifier resin consisting of a polymer or copolymer of cyclopentadiene, dicyclopentadiene, $\alpha$-pinene and/or $\beta$-pinene, an antioxydant and optionally a mineral oil, and (II) a disperse phase consisting of one or more water-swellable hydrocolloids, preferably guar gum and/or sodium carboxymethylcellulose.

The characteristic feature of the present dressing including the dressing 3 is that along all edges thereof it has a bevel 7, which causes the advantages described hereinbefore. It will be understood that this bevel necessitates that the dressing has a predetermined shape and size which, incidentally, may be arbitrarily chosen with a view to the intended purpose, and cannot be produced by simply being punched out from a sheet of dressing material. Adjacent the edge 9 of the sealing pad its thickness does not exceed $\frac{1}{4}$ of its normal thickness 8. Between the edge 9 and the bevelled portion 7 the dressing 3 in the embodiment shown has an area 13 of a constant thickness as the lesser thickness of the bevel, i.e. not exceeding $\frac{1}{4}$ of the normal thickness 8.

Figure 2:
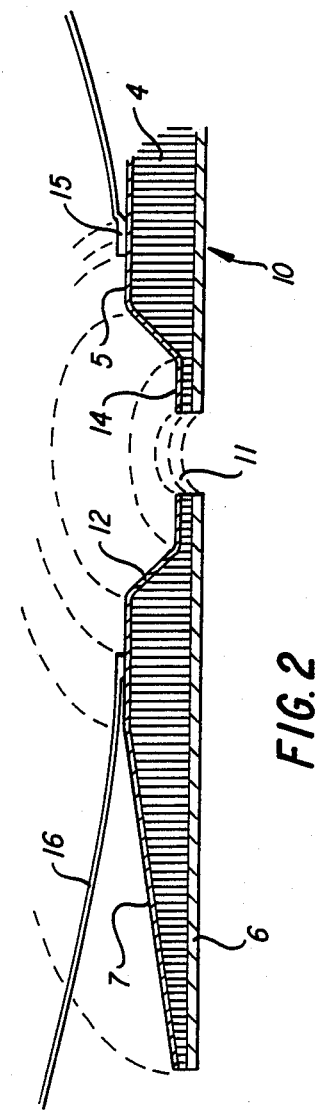
FIG. 2 shows a cross-section of an embodiment of the invention in the form of an ostomy or drainage sealing ring.

A fastening and sealing disc for ostomy or drainage equipment as shown in FIG. 2 is annular with a (not necessarily) central opening 11 for engaging a stoma or a drain (not shown). As the dressing shown in FIG. 1 it comprises a sealing pad 4 surrounded by a permanent cover layer 5 and a detachable protective cover 6 which may all be constructed as described above.

This fastening and sealing ring 10 like the dressing 3 has a bevel 7 along the outer edge and a similar bevel 12 along the inner edge, around the aperture 11. Here, however, the bevelled areas do not extend either to the outer or to the inner edges but gradually become a narrow edge area 14 in which the sealing pad has a considerably reduced thickness not exceeding $\frac{1}{4}$ of its greatest, "normal" thickness. The sealing pad of the ring 10 may, if wanted, also end from the bevelled area in a small/narrow edge area having plane-parallel areas connected to the cover layer 5 and the protecting cover 6.

In FIG. 2 it is shown how a collecting bag 16 may be fastened to the cover layer 5 of the ring by means of a weld 15.

The dimensions of dressings according to the invention may be as the dimensions of other corresponding dressings. Dressings as shown in FIG. 1 may for instance be rectangular and have a length and width from 1 or some few centimeters to 10-20 centimeters. Ostomy sealing pads may for instance be annular and have an outer diameter of 5-10 centimeters and an inner diameter of, e.g., 1 cm.

The thickness of the sealing pad or dressing, the word "pad" does not denote at any particular shape, e.g. annular or elliptical will normally be 0.25-2.5 mm. In a frequently employed thickness of 1.1 mm the width of the bevel of the embodiment shown in FIG. 1, i.e. the distance from the outer edge where it is narrowest to the portion of constant thickness, may for instance be 3-10 mm and the thickness of the thinnest area be 100-250 $\mu$m.

In case the bevel 7 and possibly the bevel 12 gradually become a thin edge area having plane-parallel or approximately plane-parallel surfaces, the thickness hereby may be as stated above, viz 100-250 $\mu$m when the maximum thickness of the sealing pad is approximately 1.1 mm.

Fastening and sealing rings for ostomy equipment are often manufactured with a smaller diameter of the central aperture than the normal outer diameter of stomas; here stomas are referred to that have a diameter within the variation of the diameter falling within the normal range (which includes approximately 98% of all cases). The purpose is that the patient or the nursing staff cut the aperture before attachment so as to exactly fit the stoma it is intended for. In such cases it is expedient according to the invention that the area of reduced thickness adjacent the aperture and between the aperture and the start of the bevel has a radial width corresponding to the area around the aperture expected to be removed when used for a stoma having a maximum width within the normal range. Typically, the diameter of the aperture will be approximately 1 cm, and within the normal range a maximum stoma diameter of approximately 4 cm is anticipated which means that the area of the sealing pad of reduced, constant thickness adjacent the aperture to stoma should have a radial width of approximately 1.5 cm. It may be appropriate that the bevel from this minimum thickness to the maximum thickness of the sealing pad is somewhat steeper along the inner edge than is the bevel along the outer edge in order for the ring to be provided with a reasonably large area—of a difference of radius not smaller than 1 cm—having full thickness. This is due to the fact that the adhesion effect and especially the duration thereof is greater in thicker than in thinner sealing pads even though, as mentioned above, an improved adhesion of the thin areas may be obtained due to the increased flexibility thereof.

The dressings according to the invention may be manufactured in various ways. A simple process is to press an object. For this one uses a plane bottom plate and a mould that has been profiled for the intended size and shape and for the intended bevel, whether a skin flange as shown in FIG. 1 or a ring as shown in FIG. 2 is to be produced. The mould may be adapted to form only one dressing at a time, or to press a number of dressings from a larger sheet of blanks in one operation. The blank or the sheet of blanks is provided with both adhesive and cover layer and is passed between the bottom plate and the mould, which is then operated to make the bevel at a pressure of e.g. 10–40 metric tons and a temperature of 90°–110° C. for 1–3 seconds; the exact conditions depend on the exact composition of the product. Then the edges are cut clean by die-cutting in a well-known manner. During the pressing the protective cover must be present.

It is also possible to die-cast the dressings of the invention. Thereby a web of material for the cover layer and a web of, e.g., siliconized paper or slip-film of polyethylene which may for instance be deformed without significant reduction of the slip-properties, are led across a injection casting mould.

The casting mould has a hollow space between the two siliconized sheets, corresponding to the intended shape of the dressing (skin plate or ring) and the bevel thereof and is provided with an inlet for adhesive. The mass is hereby cast at a suitable temperature after which the two sheets are removed together one step from the casting mould, the dressing with cover layer and protective cover thus formed is detached and cut clean by die-cutting as mentioned above.

It goes without saying that the cover layer for rings to be used for ostomy equipment and drainage equipment with bags must be capable of being welded to the film from which the collecting bag has been produced. Especially suitable for this purpose are films made from polyvinylidenechloride or laminates containing same.

What is claimed:

1. A dressing of the kind comprising a skin-friendly, water absorbent sealing pad adhering to skin and mucous membranes and having a predetermined shape and size, said dressing consisting of at least one hydrocolloid selected from the group consisting of water-soluble and water-swellable hydrocolloids, the hydrocolloid being admixed with a water-insoluble, viscous, elastomeric binder, said sealing pad on one surface being firmly connected to a non-adhesive, water-tight cover layer and on the other surface being provided with a detachable protective cover, the sealing pad extending at least to the outer edges of the cover layer, comprising the improvement that the sealing pad is bevelled at least along all outer edges in the thickness dimension such that its thickness adjacent the edge does not exceed ¼ of the thickness of the sealing pad in its non-bevelled portions.

2. A dressing as claimed in claim 1, wherein an area of a constant thickness of at most ¼ of the maximum thickness of the sealing pad is situated between the thinnest portion of the bevel and the edge of the dressing.

3. A dressing as claimed in claim 1, said dressing being annular, adapted for securing ostomy or drainage equipment and provided with an aperture intended for engaging a stoma or a drain, wherein the sealing pad is also bevelled along the edge of the aperture.

4. A dressing as claimed in claim 3 in the form of a fastening and sealing ring for ostomy equipment, in which the opening for engaging a stoma has a diameter smaller than the normal diameter of stomas and is adapted to be enlarged to fit a given stoma by the removal of material from the sealing pad and the cover layer, wherein the area of reduced thickness adjacent the aperture has a radial width corresponding to the area around the aperture expected to be removed when used for stomas having a maximum diameter within the normal range.

5. A dressing as claimed in claim 3, wherein an area of a constant thickness of at most ¼ of the maximum thickness of the sealing pad is situated between the thinnest portion of the bevel and the edge of the dressing.

* * * * *